(12) United States Patent
Heinrich

(10) Patent No.: US 11,772,014 B2
(45) Date of Patent: Oct. 3, 2023

(54) BIOLOGICAL MATERIAL COLLECTION AND SEPARATION SYSTEM AND METHODS OF USE

(71) Applicant: Hans-Werner Heinrich, Spring Valley, CA (US)

(72) Inventor: Hans-Werner Heinrich, Spring Valley, CA (US)

(*) Notice: Subject to any disclaimer, the term of this patent is extended or adjusted under 35 U.S.C. 154(b) by 0 days.

(21) Appl. No.: 17/974,370

(22) Filed: Oct. 26, 2022

(65) Prior Publication Data

US 2023/0039229 A1 Feb. 9, 2023

Related U.S. Application Data

(63) Continuation of application No. 17/133,393, filed on Dec. 23, 2020, now Pat. No. 11,504,653, which is a continuation-in-part of application No. 16/691,386, filed on Nov. 21, 2019, now Pat. No. 11,344,880.

(60) Provisional application No. 62/953,574, filed on Dec. 25, 2019, provisional application No. 62/773,417, filed on Nov. 30, 2018.

(51) Int. Cl.
*B01D 21/26* (2006.01)
*B01L 3/00* (2006.01)
*B01L 3/02* (2006.01)

(52) U.S. Cl.
CPC .......... *B01D 21/262* (2013.01); *B01L 3/0293* (2013.01); *B01L 3/5021* (2013.01); *B01L 2300/042* (2013.01)

(58) Field of Classification Search
CPC ... B01D 21/262; B01L 3/0293; B01L 3/5021; B01L 2300/042
See application file for complete search history.

(56) References Cited

U.S. PATENT DOCUMENTS

| | | | | |
|---|---|---|---|---|
| 3,837,376 A | * | 9/1974 | Brown | B01L 3/5021 141/330 |
| 4,346,608 A | * | 8/1982 | Olenick | B01L 3/0293 422/82 |
| 4,640,785 A | * | 2/1987 | Carroll | G01N 33/491 435/2 |
| 4,832,851 A | * | 5/1989 | Bowers | B01D 61/18 422/534 |
| 5,114,033 A | * | 5/1992 | Golias | B01L 3/0293 222/479 |
| 2007/0161491 A1 | * | 7/2007 | Jinno | B01L 3/5021 494/16 |

* cited by examiner

*Primary Examiner* — Liam Royce
(74) *Attorney, Agent, or Firm* — Baumgartner Patent Law; Marc Baumgartner

(57) ABSTRACT

A system for collecting and separating biological material includes a centrifuge tube, a separation tube having an open bottom, a cap, a plug for temporarily sealing the open bottom of the separation tube, and a separation medium disposable within the centrifuge tube. The centrifuge tube and the separation tube sealingly and releasably couple to the cap, such that, when coupled, the separation tube is positioned within the centrifuge tube. The cap is configured to facilitate and/or regulate the introduction of air, gas, or other matter into the separation tube. When fully sealed, the separation tube may be placed under a vacuum condition, whereby a needle apparatus is used to facilitate introduction of matter into the separation tube. When the separation tube is positioned within the centrifuge tube, the bottom portion of the separation tube is submersed in the separation medium.

14 Claims, 21 Drawing Sheets

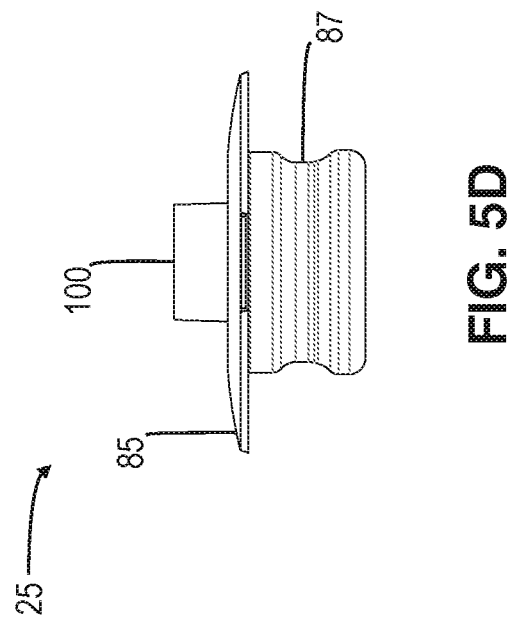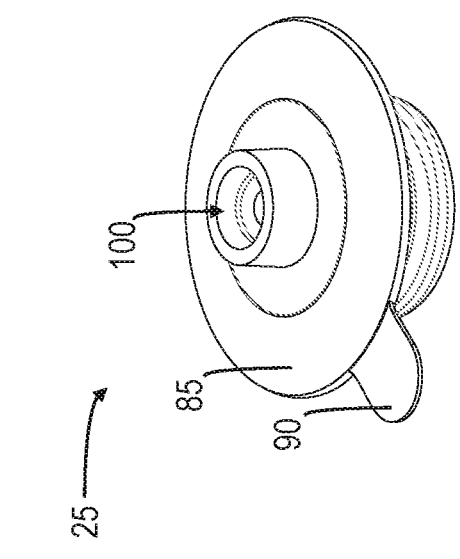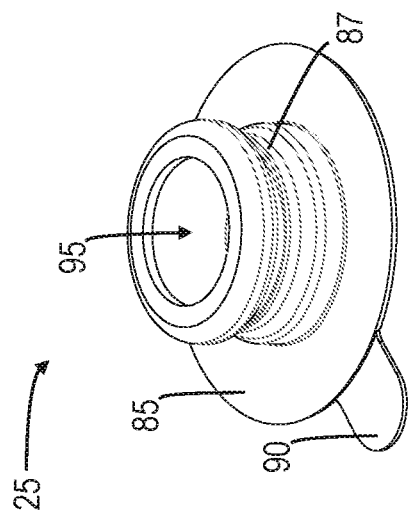

BIOLOGICAL MATERIAL COLLECTION AND SEPARATION SYSTEM AND METHODS OF USE

CROSS-REFERENCE TO RELATED APPLICATION(S)

This application is a continuation of U.S. patent application Ser. No. 17/133,393, filed Dec. 23, 2020, which claims the benefit of priority to U.S. Provisional Application No. 62/953,574, filed Dec. 25, 2019, and which is also a continuation-in-part of U.S. Non-Provisional patent application Ser. No. 16/691,386, filed Nov. 21, 2019, which claims the benefit of priority to U.S. Provisional Application No. 62/773,417, filed Nov. 30, 2018, the entire disclosures of each of which are incorporated by reference herein.

BACKGROUND OF THE INVENTION

1. Field of Invention

The present invention relates to systems, apparatuses, and methods for isolating biological material from samples, such as biological fluids, dispersed tissue specimens, and cultured cells.

2. Description of Related Art

The separation of certain cells or cell population(s) from complex biological liquids such as blood is a routine procedure in many fields of medical research. Many different processes are available and are commonly used in the research community for isolating target cells.

Centrifuging anti-coagulated blood leads to the separation of red blood cells and white blood cells. The lighter white blood cells sediment slowly and form an opaque layer on top of the red blood cells. This layer is commonly referred to as the "buffy coat". Several washing steps are normally necessary to remove the red blood cells. This process was for many years the standard procedure for isolating lymphocytes from blood.

The introduction of a separation medium with the specific density of the white blood cells, i.e., a density separation medium, makes it possible to separate white blood cells from red blood cells by centrifugation of anti-coagulated whole blood through the density separation medium. The heavier red blood cells sediment through the density separation medium, while the white blood cells remain on top of the density separation medium. The white blood cell layer can then be carefully removed with a pipette. However, this results in additional stress to living cells. This remains the standard procedure in isolating white blood cells from blood specimens today.

U.S. Pat. No. 4,832,851 A discloses an apparatus for filtering blood. The apparatus includes a filter vessel with a filter disposed at the open lower end, whereby the open lower end is inserted into a container having a closed lower end and a capped upper end. The capped neck of the filter vessel is formed with a capillary channel for pressure equalization. Among other things, this reference does not teach a cap for suspending filter vessel inside the container, whereby the cap is designed with a means to regulate, or to facilitate the regulation of, pressure within the filter vessel.

U.S. Pat. No. 9,764,079 B2 discloses an isolation system for white blood cells from blood. The system includes a capped separation tube having open access that can be placed inside a centrifuge tube with a cap and closed bottom. During centrifugation, the small cell pellets sediment at the bottom of the centrifuge tube and the white blood cells remain inside the separation tube. Among other things, this reference does not teach that the separation tube is submersed in separation medium or that the cap is designed with a means to regulate, or to facilitate the regulation of, pressure within the separation tube.

U.S. Pat. No. 10,040,064 B1 discloses a centrifuge tube assembly to extract blood components. An inner tube has a lower open end and an open upper end in the form of a threaded male luer that is closed by a cap. The inner tube extends through the cap of an outer containment tube. During centrifugation, light density components move towards the cap and the heaviest components collect at the bottom of the inner tube. Among other things, this reference does not teach that the inner tube is submersed in separation medium or that the cap is designed with a means to regulate, or to facilitate the regulation of, pressure within the inner tube.

U.S. Pat. No. 4,315,892 A discloses a fluid collection device for separating blood into its phases. An outer container has an open top closed by a cap. A phase partitioning device containing a sealant is disposed within the outer tube. During centrifugation, the cellular phases separate and the sealant is dispensed from the phase partitioning device to form a semi-rigid partition between the phases. Among other things, this reference does not teach an open-bottom inner containment unit suspended within the outer tube by attachment to the cap, whereby the cap is designed with a means to regulate, or to facilitate the regulation of, pressure within the inner containment unit.

US 2014/0349828 A1 discloses a centrifuge vessel that includes a collector having an open end and a cap. The vessel contains a fraction-density-altering solution and a blood sample. During centrifugation, the blood sample separates into its respective portion of target material based on density and the target material such as circulating tumor cells and blood cells are moved from the vessel to the collector. Among other things, this reference does not teach a cap used to fix the collector inside the vessel or that the cap is designed with a means to regulate, or to facilitate the regulation of, pressure within the collector.

U.S. Pat. No. 4,683,058 A discloses a filter assembly for the separation of blood. The assembly includes a centrifuge tube that includes a filter tube having a cap to seal the upper end and a filter at an opposite open end. Among other things, this reference does not teach that a lower end of the filter tube is submersed in separation medium or that the cap is designed with a means to regulate, or to facilitate the regulation of, pressure within the filter tube.

U.S. Pat. No. 6,835,353 B2 discloses a centrifugally-driven assembly for separating blood product. The assembly includes a tubular receptacle and a closure for supporting a port having a second cap. Among other things, this reference does not teach that the second cap is designed with a means to regulate, or to facilitate the regulation of, pressure within the system, namely the ports or pipes extending therefrom.

U.S. Pat. No. 6,516,953 B1 discloses a rigid tube having a closure comprising a tubular seal plug that includes a septum and a central passage. The seal plug separates the blood samples into higher and lower density components. Among other things, this reference does not teach an open-bottom inner containment unit suspended within the outer tube by attachment to the tube closure, whereby the tube closure is designed with a means to regulate, or to facilitate the regulation of, pressure within the inner containment unit.

US 2004/0166029 A1 discloses a device for separating blood components. The device includes a separator having an open bottom end and a bellow for closing the top end. The separator is disposed inside an outer container. Among other things, this reference does not teach an open-bottom inner containment unit suspended within the outer tube by attachment to the cap, whereby the cap is designed with a means to regulate, or to facilitate the regulation of, pressure within the inner containment unit.

U.S. Pat. No. 4,436,631 A discloses a system for the separation of blood samples. The system includes an outer centrifuge tube containing a wash solution and an inner tube which is insertable into the outer tube. The system separates blood samples, based on the densities of the various components. The inner tube includes an air vent to allow free communication between a lower inner area and the atmosphere. Among other things, this reference does not teach a cap designed with a means to regulate, or to facilitate the regulation of, pressure within the inner tube.

Blood samples are routinely drawn using a system that employs an evacuated tube. One such system is the BD Vacutainer® System by BD Biosciences. Evacuated systems allow low risk blood drawing, safe handling of the samples, standardization of the related processes and safe discard of biohazardous specimens. Once collected, the sample must be processed. For example, the separation of certain cells from blood for research and diagnostic purposes requires open handling of the drawn anticoagulated blood sample.

Based on the foregoing, there is a need in the art for an apparatus and system that provides a means for isolating target material from non-target material, combined with a means for regulating air pressure within the system to allow for controlled release and analysis of the isolated target material, thus minimizing the number of processes/steps for isolation and collection and, hence, mitigating stress to the target material.

SUMMARY OF THE INVENTION

A system for separating biological material includes a centrifuge tube, a separation tube having an open bottom, a cap, a plug for sealing an open bottom of the separation tube, and a separation medium disposable within the separation apparatus. The centrifuge tube and the separation tube are configured to sealingly and releasably couple to the cap. The cap is configured to facilitate and/or regulate air- or gas-flow between an area outside of the cap and an interior of the separation tube. A volume of the separation medium is such that, when the separation tube and the centrifuge tube are coupled to the cap, the bottom of the separation tube is submersed in the separation medium.

The plug is configured to disengage from the separation tube during centrifugation. In some embodiments, the plug is configured to displace into the separation tube upon disengagement from the open bottom; whereas, in other embodiments, the plug is configured to displace into the centrifuge tube upon disengagement from the open bottom.

In various embodiments, when the top and bottom openings of the separation tube are sealed, an interior of the separation tube is evacuated. Where an evacuated separation tube is employed, a needle apparatus for drawing fluid therethrough is used to introduce material into the separation tube. For example, a needle of a blood-drawing apparatus may be inserted into a patient's vein, and another needle of the blood-drawing apparatus may be punctured through the cap, whereby the vacuum within the separation tube draws the blood sample through the needle apparatus into separation tube. The blood flow stops at a certain volume, i.e., when the pressure within separation tube equals the blood pressure in the vein. In various embodiments, an anticoagulant is disposed within the separation tube to prevent blood entering separation tube from clotting.

In an embodiment, an aperture extends through the top of the cap and opens into an interior portion, i.e., a cavity, of the cap, such that, when the cap is coupled to the separation tube, the cap provides open communication between an area outside of the cap and an interior of the separation tube. In a further embodiment, the cap includes one or more channels that extend through the top of the cap, such that, when the cap is coupled to the separation tube, the channels provide open communication between an area adjacent to the top of the cap and an interior of the separation tube.

In an embodiment, the system further includes a plug configured to releasably seal the cap's aperture and channels. The lower portion of the cap plug is insertable into the aperture and is configured to seal the aperture. The upper portion of the cap plug includes a flange. In an embodiment, the flange is configured to transition between a closed position and an open position. In the closed position, the flange is configured to seal the channels, and in the open position, the flange is configured to unseal, i.e., open, the channels to provide open communication between the interior of the separation tube and an area outside of the cap. In an embodiment, the upper portion of the cap plug is a mechanical actuator configured to transition the flange between the open position and the closed position.

In an embodiment, the cap plug is releasably retained within the cap by an interference fit between the lower portion of the cap plug and an interior surface of the cap and/or the interior wall of the separation tube. In a further embodiment, a groove extends around the lower portion of the cap plug. The groove is configured to matingly engage a retaining lip protruding from the upper portion of the cavity, whereby the retaining lip seats into the groove to facilitate a snap fit between the cap plug and the cap. In addition to the interference fit, this serves to further assist in releasably coupling the cap plug to the cap.

In an embodiment, the system also includes a hollow needle coupled to a means for regulating a flow of air, gas, or other matter. The needle is insertable through the cap or cap plug, and is used to facilitate the introduction of air, gas, or other matter into the separation tube. Example means for regulating a flow of air, gas, or other matter include, but are not limited to, a syringe, a pump, and an air compressor.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

FIGS. 5A-5D show various views of the plug, according to an embodiment of the present invention;

Figure 9A:
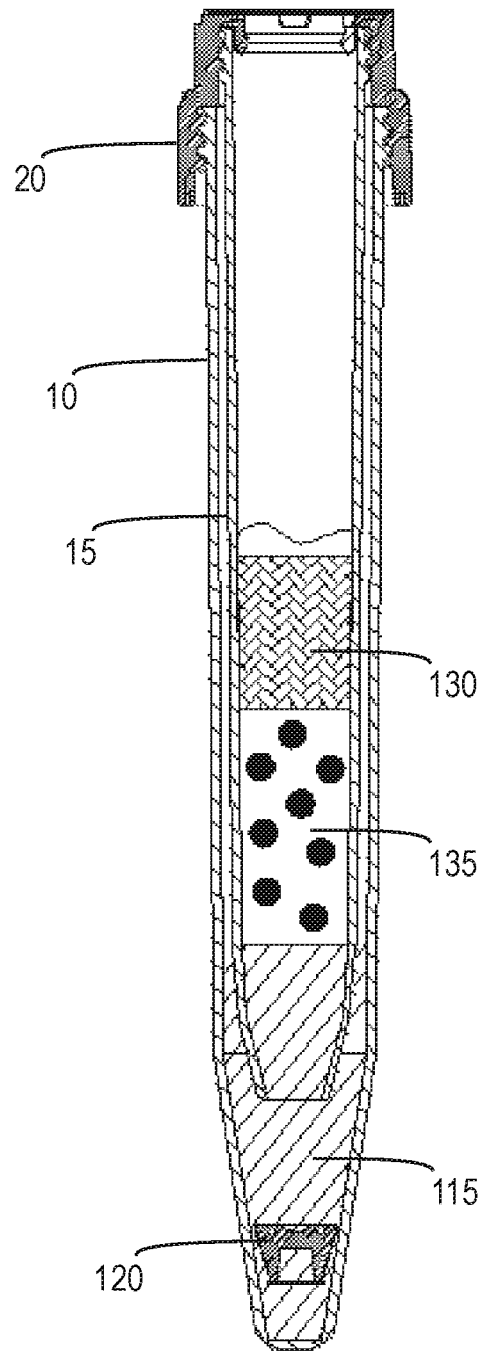
Figure 9B:
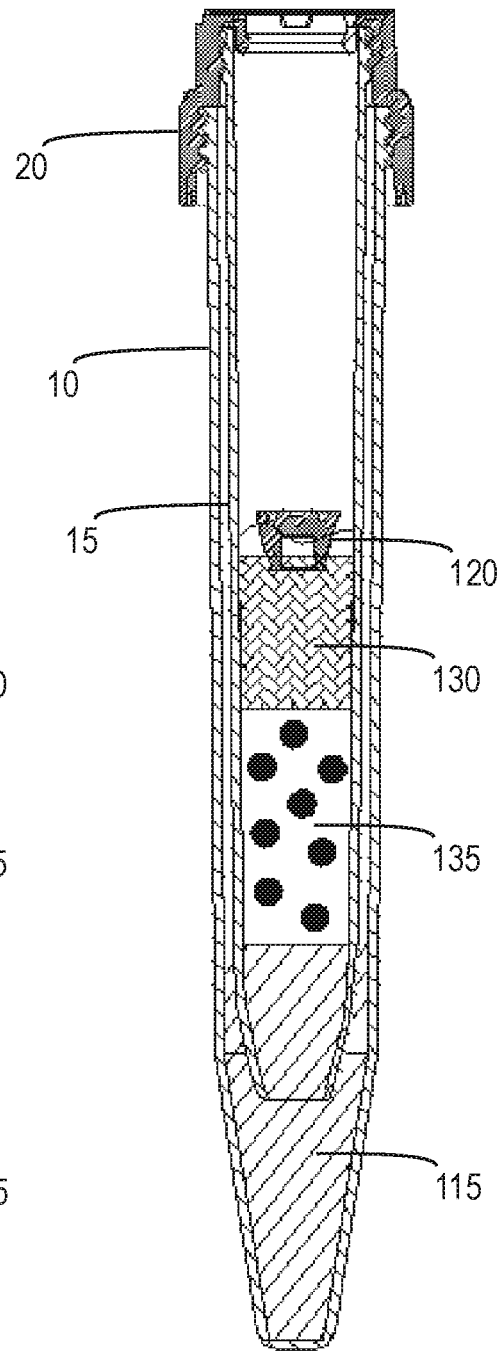
Figure 10:
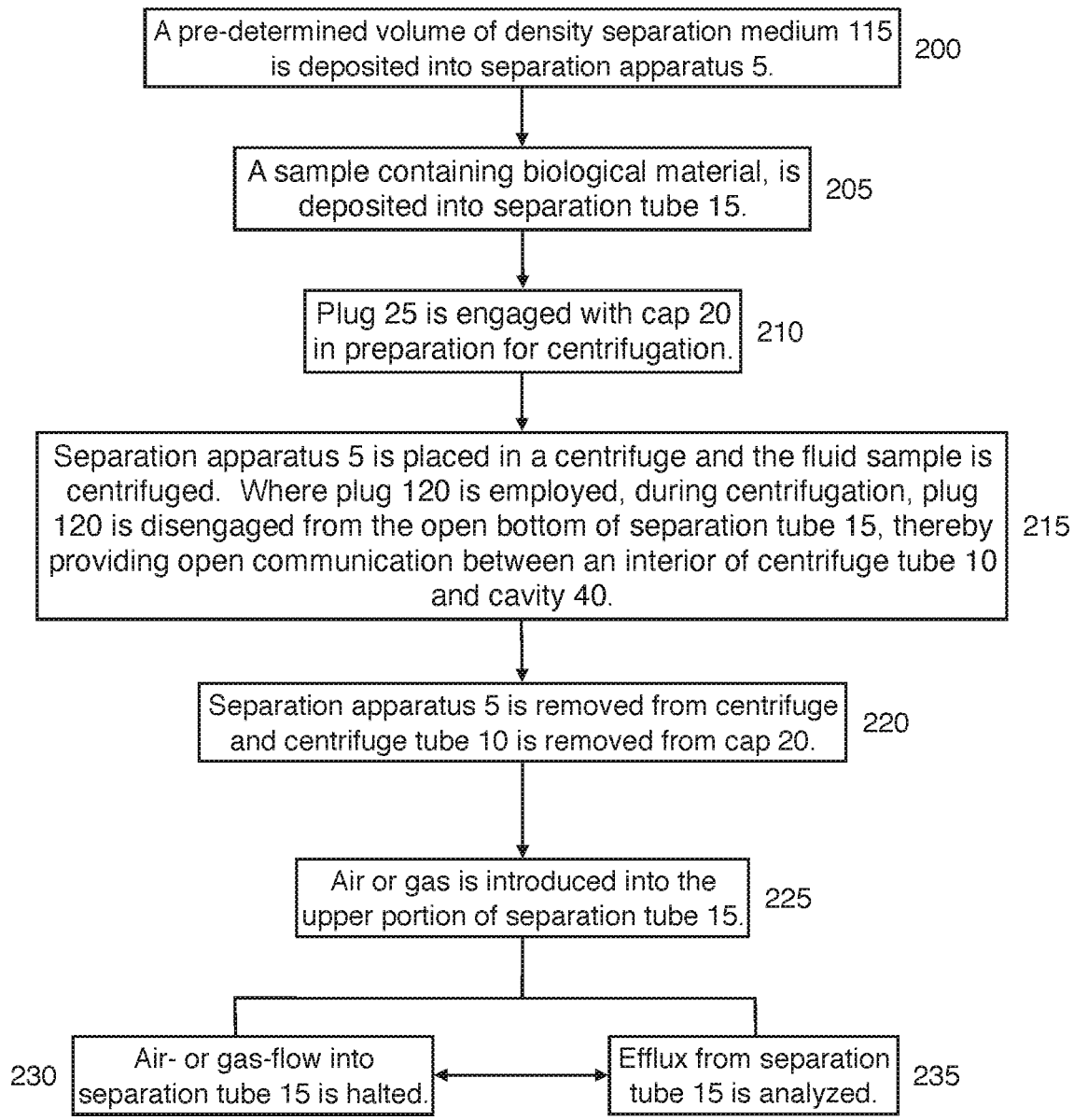
Figure 11A:
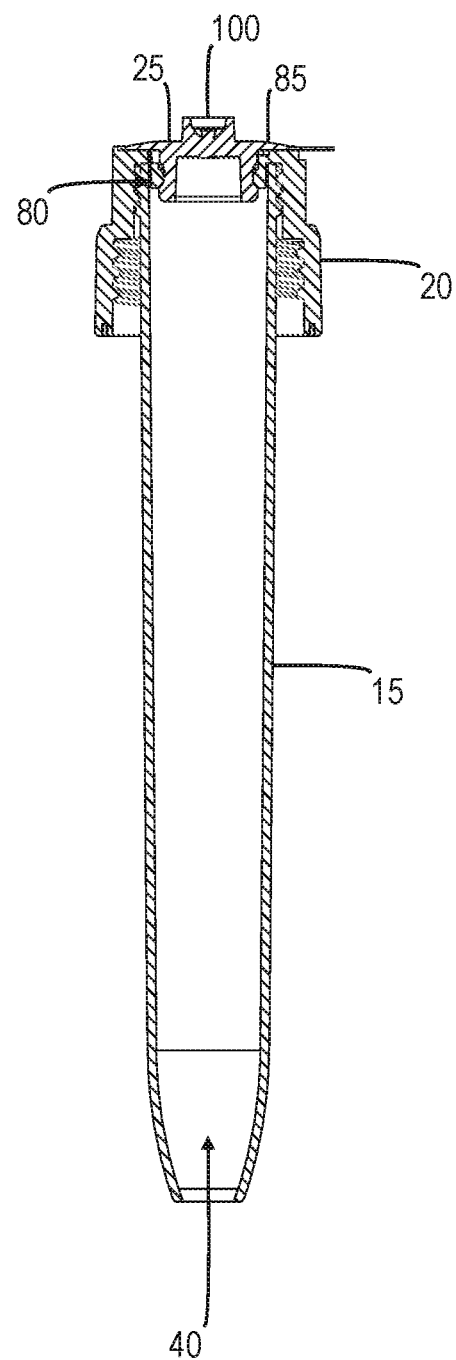
Figure 11B:
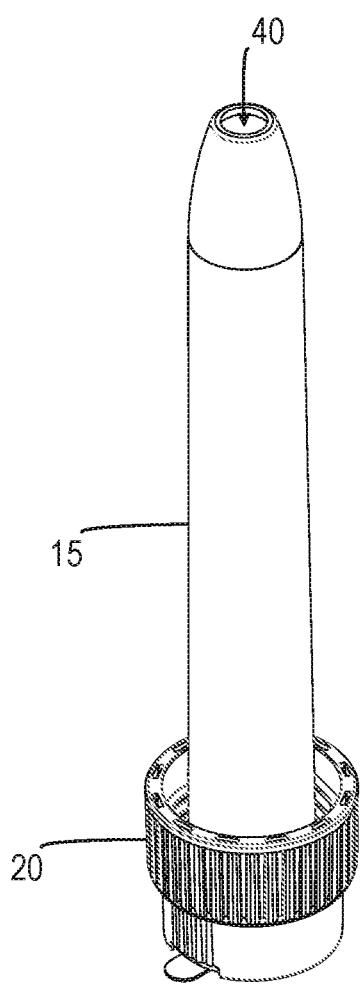
Figure 11C:
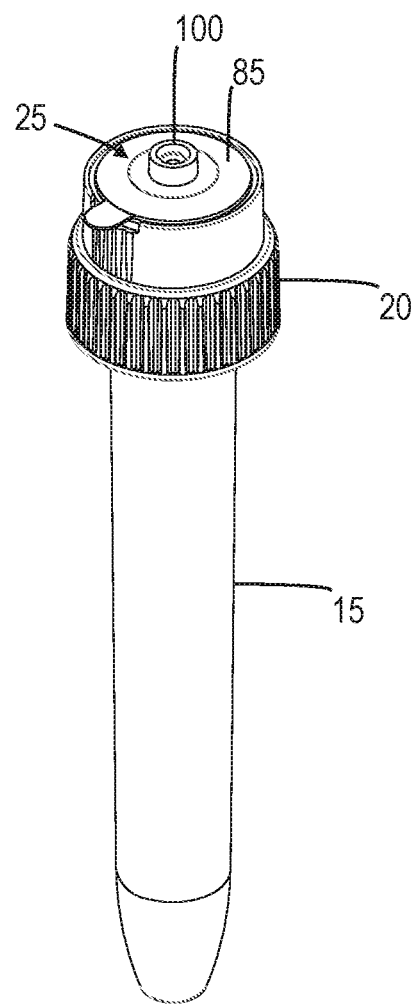
Figure 12A:
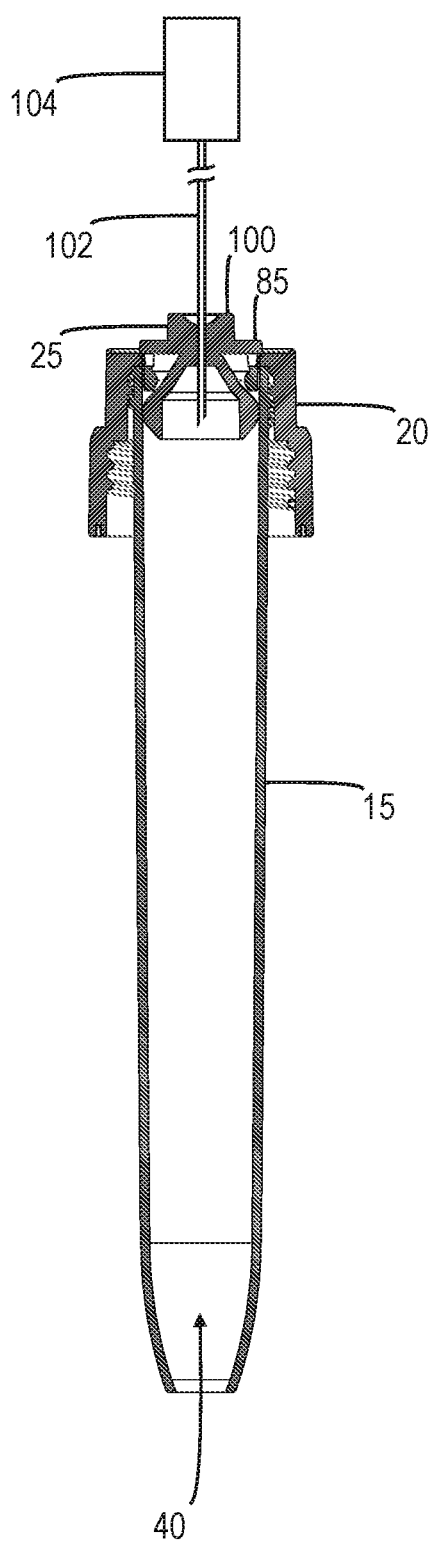
Figure 12B:
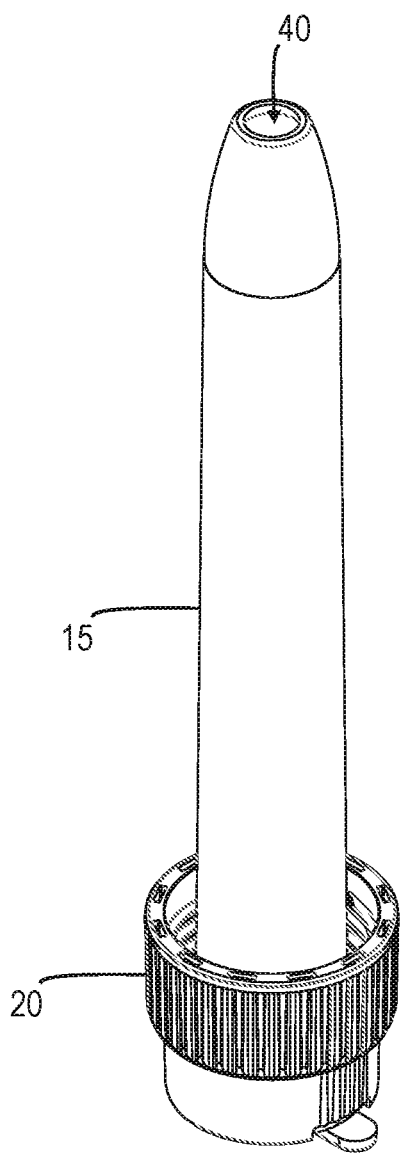
Figure 12C:
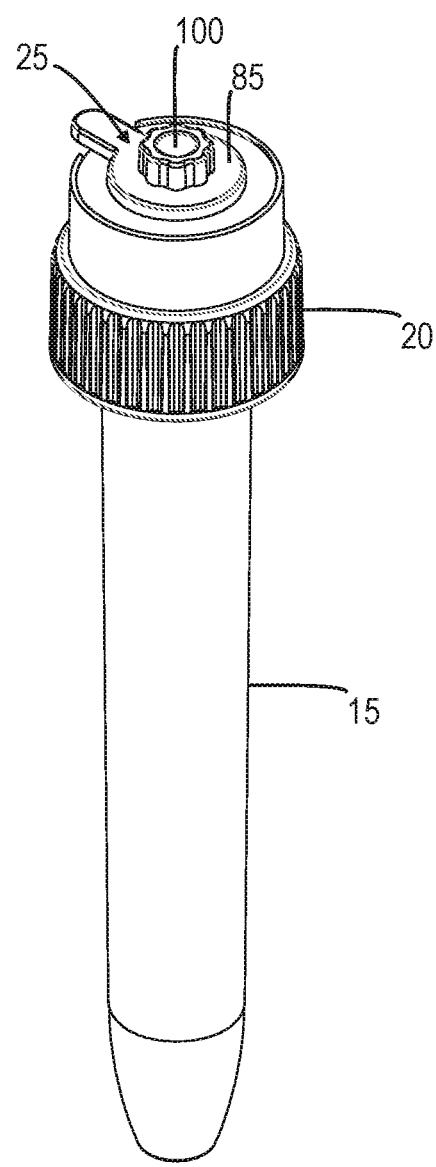

FIG. SB shows a cross-sectional view of the collection and separation apparatus, according to an embodiment of the present invention;

FIGS. 9A-9B show cross-sectional views of the collection and separation apparatus post-centrifugation, according to an embodiment of the present invention;

FIG. 10 is a flow chart showing a method of using the separation system, according to an embodiment of the present invention;

FIGS. 11A-11C show various views of the separation tube, the cap, and the plug in an assembled form, according to an embodiment of the present invention;

FIG. 12A shows a sectional view of the separation tube, the cap, and the plug with the needle and the regulator, according to an embodiment of the present invention; and FIGS. 12B-12C show the separation tube, the cap, and the plug in an assembled form, according to an embodiment of the present invention.

DETAILED DESCRIPTION OF PREFERRED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B, and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Preferred embodiments of the present invention and their advantages may be understood by referring to FIGS. 1A-11, wherein like reference numerals refer to like elements.

With reference to FIGS. 1A-1D, separation apparatus 5 includes centrifuge tube 10, separation tube 15, and cap 20 (with or without plug 25), each of which are further individually illustrated in FIGS. 2-6C.

Figure 2:
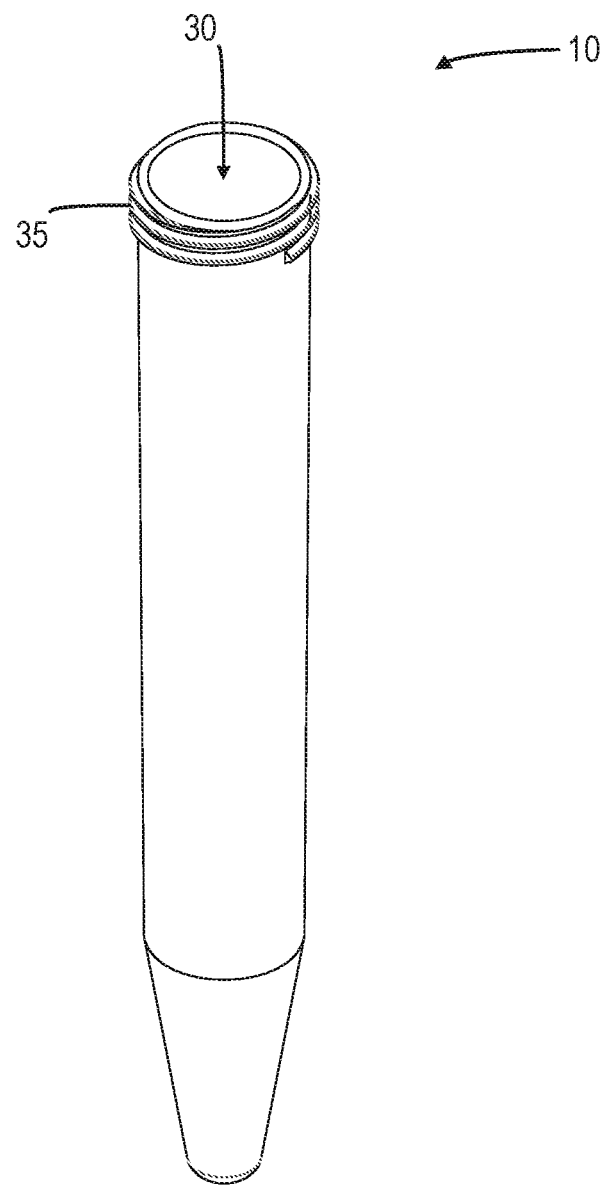
FIG. 2 shows a perspective view of the centrifuge tube, according to an embodiment of the present invention.

With reference to FIG. 2, centrifuge tube 10 has an open top that opens into cavity 30. The bottom of centrifuge tube 10 is closed. Connector 35 is disposed at an upper portion of centrifuge tube 10.

Figure 3A:
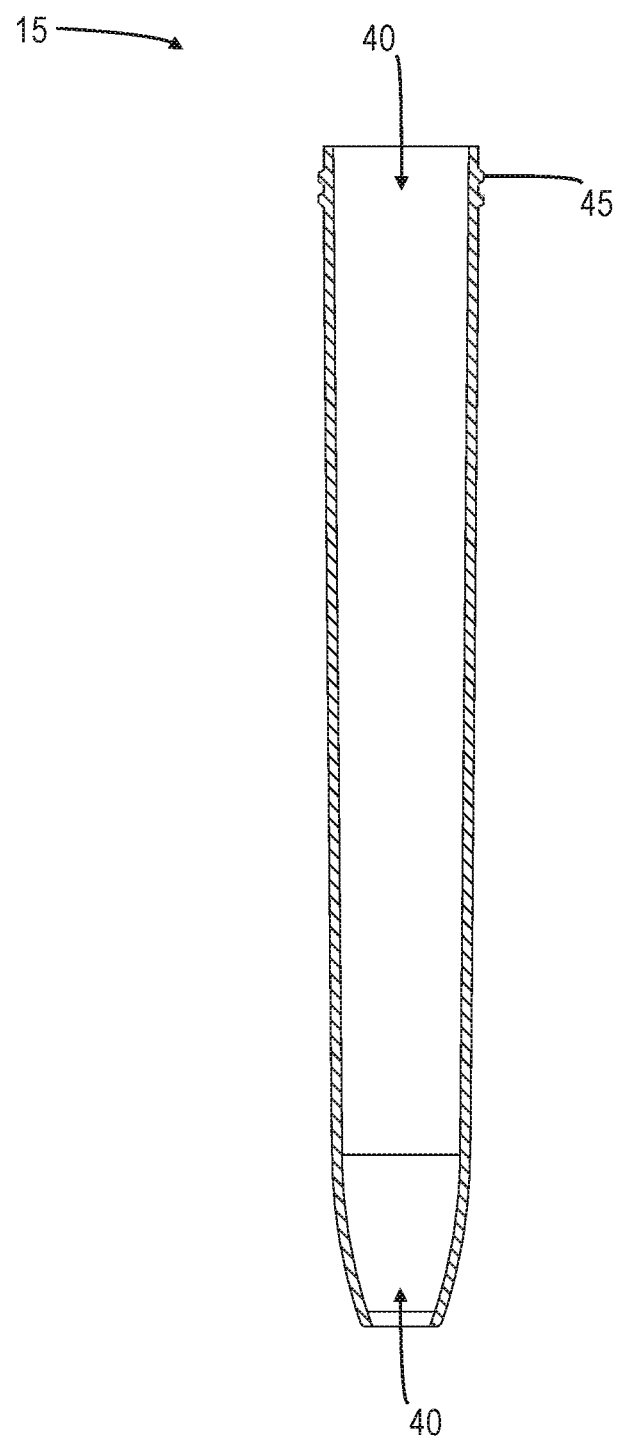
FIGS. 3A-3C show various views of the separation tube, according to an embodiment of the present invention.
Figure 3C:
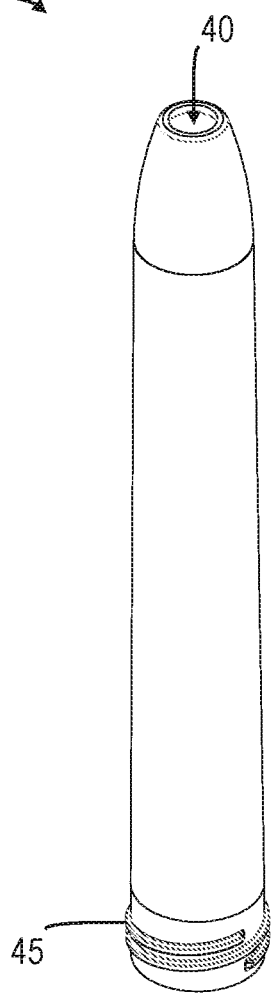
Figure 3B:
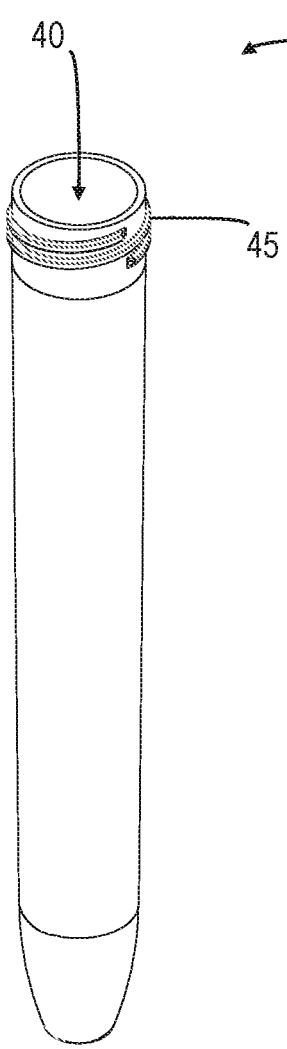
Figure 4A:
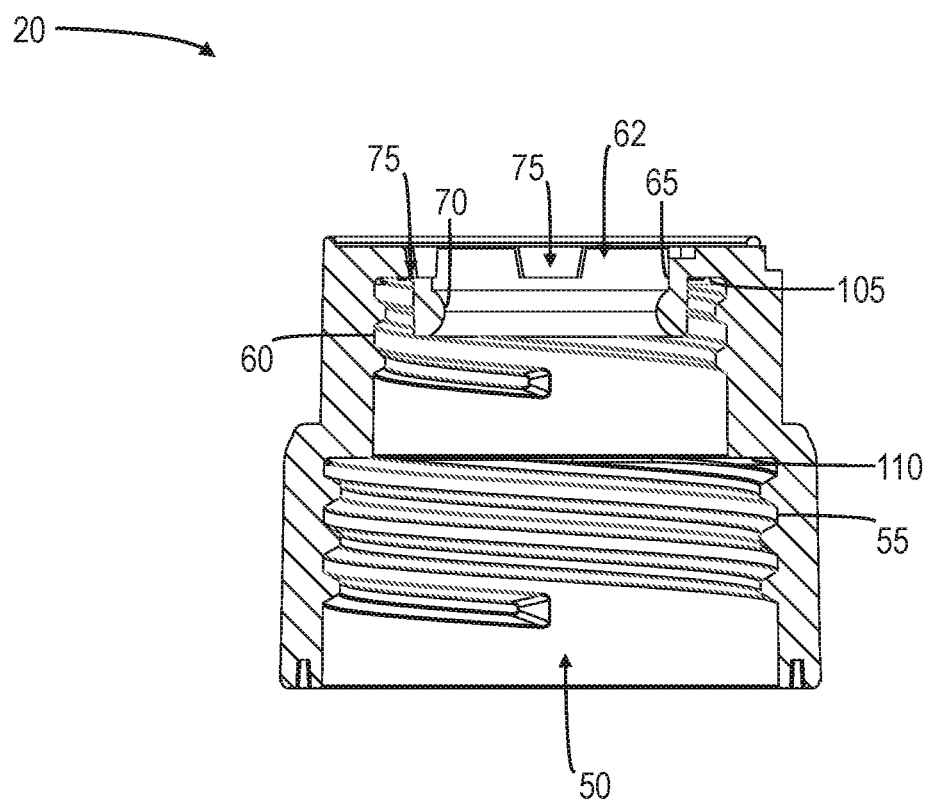
FIGS. 4A-4D show various views of the cap, according to an embodiment of the present invention.
Figure 4C:
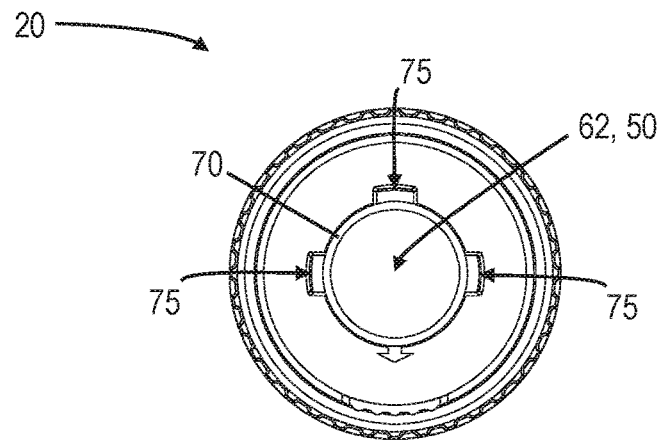
Figure 4B:
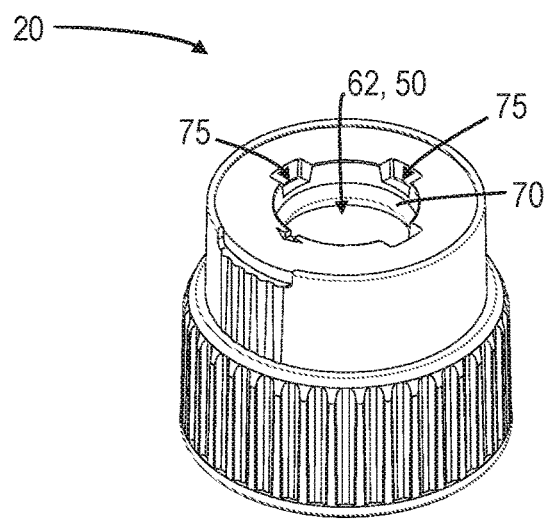
Figure 4D:
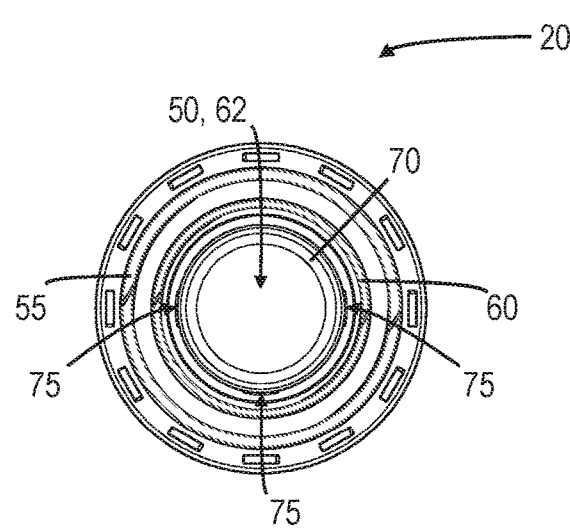
Figure 5A:
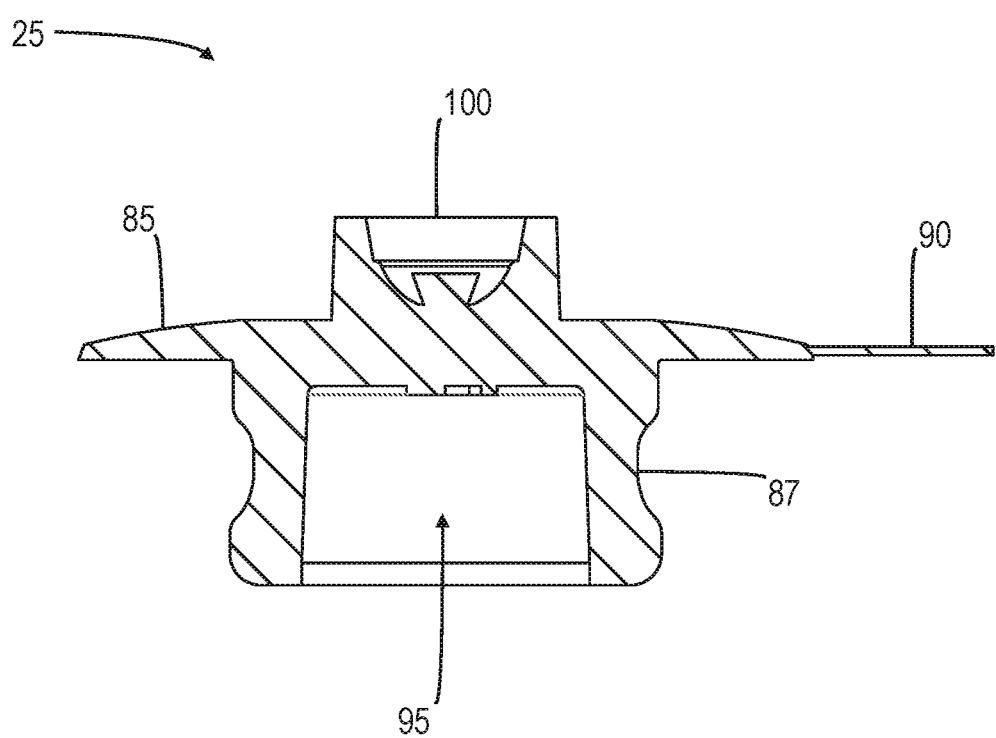

With reference to FIGS. 3A-3C, separation tube 15 has an open top and an open bottom, each of which open into hollow interior 40. Connector 45 is disposed at an upper portion of separation tube 15. With additional reference to FIG. 2, the figures depict connectors 35, 45 as threading that extends around an outer circumference of an upper portion of centrifuge tube 10 and separation tube 15, respectively. However, one skilled in the art would understand and appreciate that alternative connection means could be employed to serve the same function.

With reference to FIGS. 4A-4D, cap 20 has an open bottom that opens into cavity 50. Cavity 50 includes connectors 55, 60 configured to matingly engage connectors 35, 45, respectively, to releasably couple centrifuge tube 10 and separation tube 15 to cap 20. Aperture 62 extends through the top surface of cap 20 and opens into cavity 50. Cavity neck 65 is disposed adjacent to, and is set inward from, connector 55. In an embodiment, retaining lip 70 protrudes from a lower portion of cavity neck 65. In an assembled state, wherein separation tube 15 is coupled to an unplugged cap 20, cap 20 provides open communication between an area outside of separation apparatus 5 and hollow interior 40.

Figure 1A:
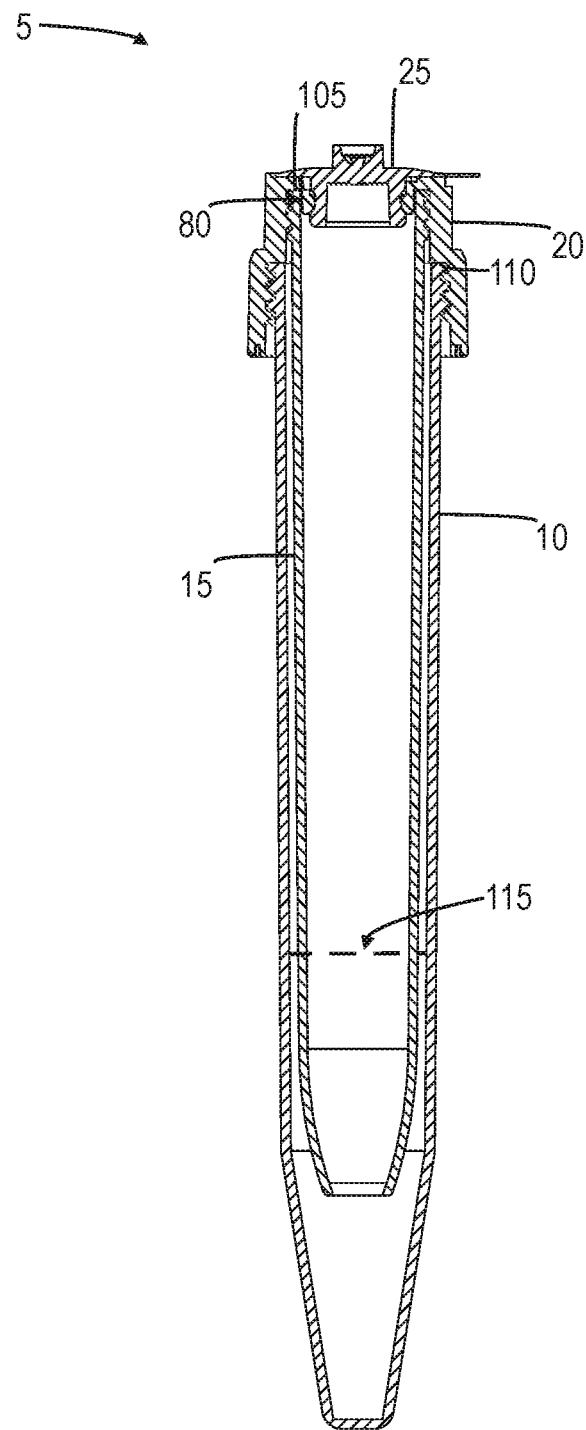
FIGS. 1A-1D show various views of the separation apparatus, according to an embodiment of the present invention.
Figure 1B:
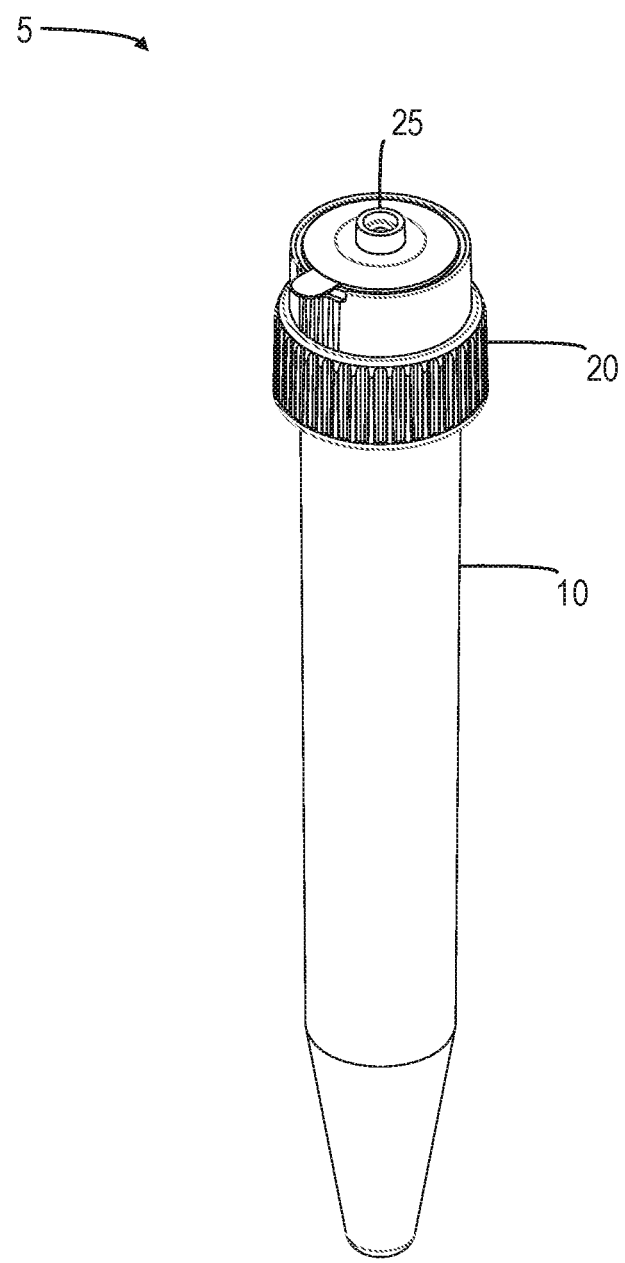
Figure 1C:
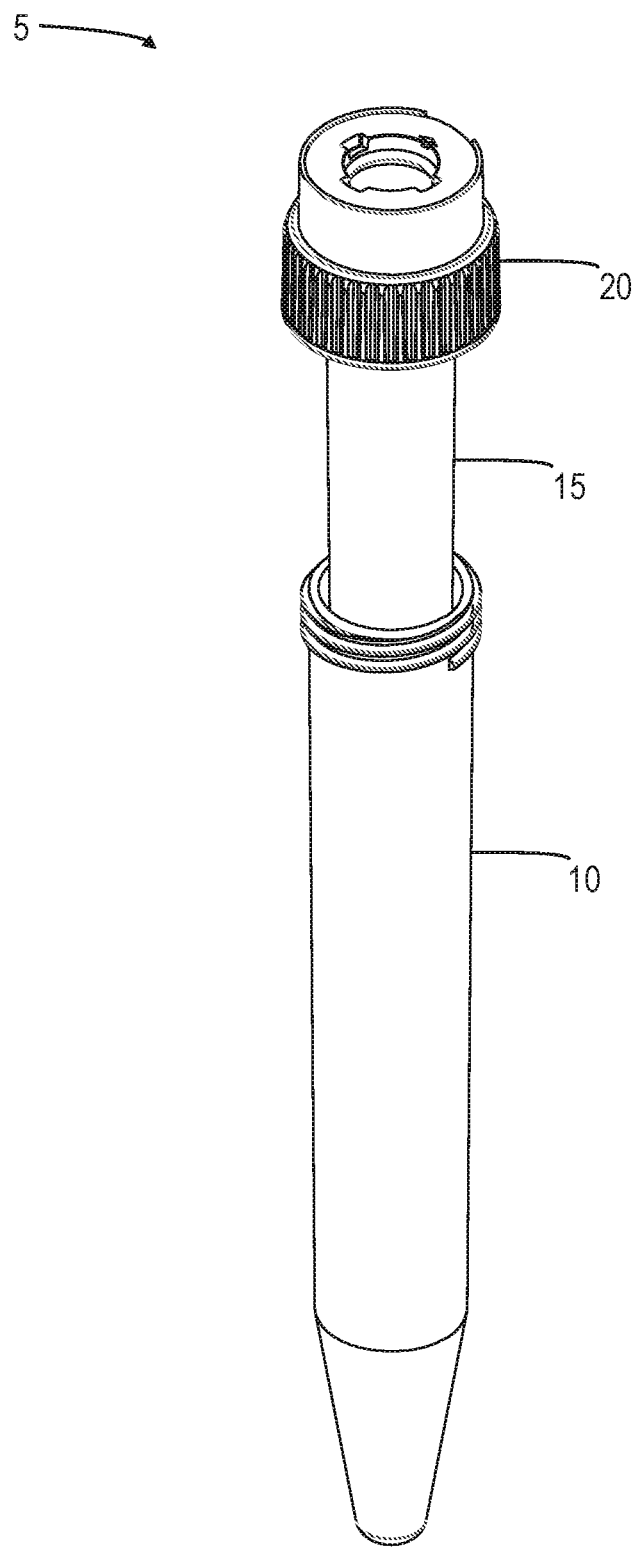
Figure 1D:
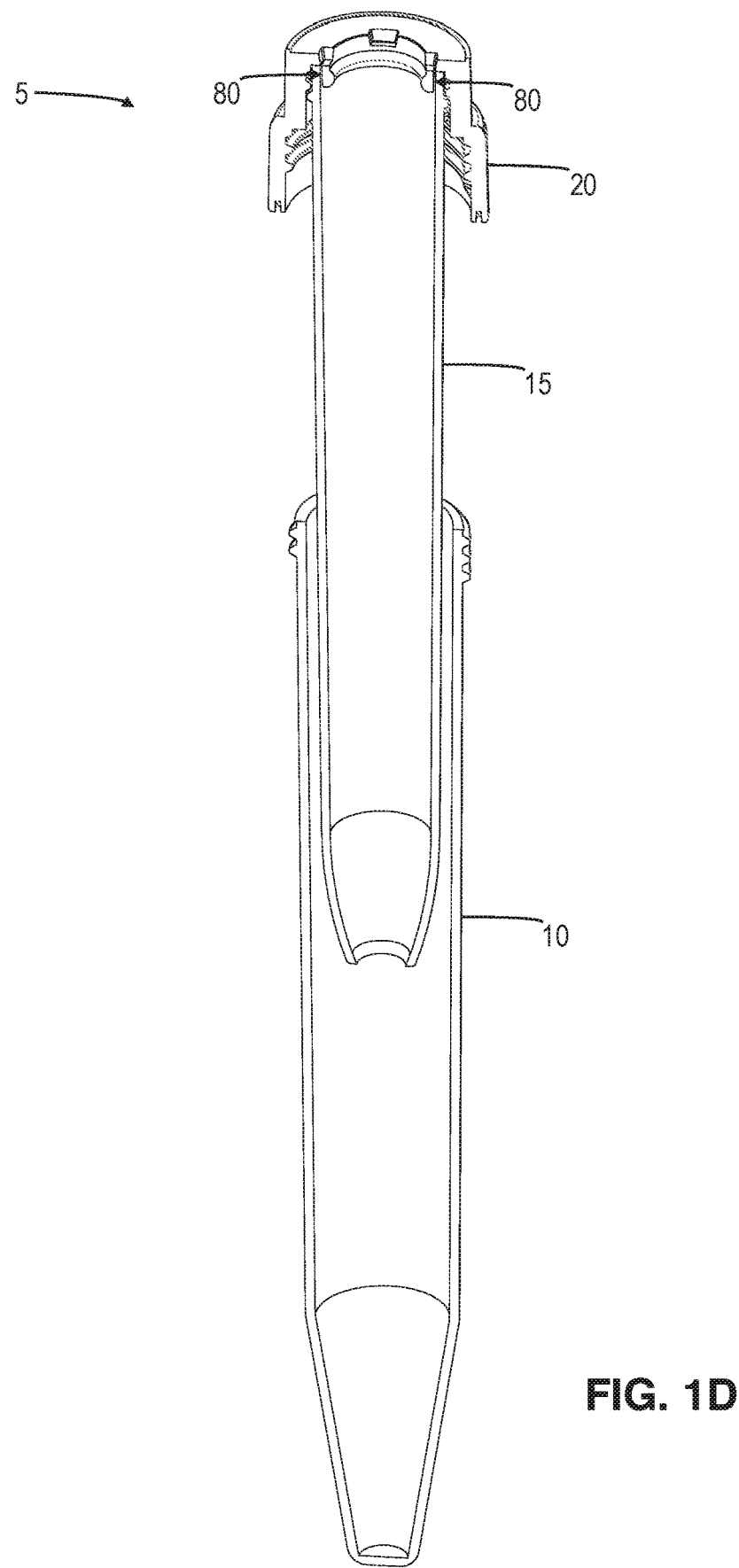

In an embodiment, one or more channels 75 extend through top surface of cap 20. In an assembled state, wherein separation tube 15 is coupled to cap 20 (plugged or unplugged), channels 75 provide open communication between the top of cap 20 and cavity 40. In other words, channels 75 serve as a bypass for influent air to travel to cavity 40 when cavity 50 is otherwise sealed. For example, in an embodiment, as shown in FIGS. 1A, 1D and 7A, when separation tube 15 is coupled to cap 20, the interior wall of separation tube 15 is separated from a rear surface of cavity neck 65 by open space 80. Channels 75 pass through cap wall and open into open space 80, allowing air to travel into and through open space 80 without passing through aperture 62.

With reference to FIGS. 5A-6C, plug 25 includes flange 85 that extends from an outer circumference of plug 25. The bottom surface of flange 85 is configured to complement the contour the top surface of cap 20. For example, in a preferred embodiment, the bottom surface of flange 85 is disposed orthogonal to flange's central axis, allowing it to seat onto and create an air-tight seal with the top surface of cap 20. Pull tab 90 extends from an outer edge of flange 85 and facilitates removal of plug 25 from cap 20.

Lower portion of plug 25, i.e., the portion of plug 25 below flange 85, includes cavity 95 and is configured to be received into cavity 50. Upon insertion, lower portion of plug 25 is removably retained within cavity 50 via an interference, i.e., friction, fit between lower portion of plug 25 and the wall surface of cavity neck 65 and/or the inner wall of separation tube 15 to create a sealed, i.e., air-tight, engagement between plug 25 and cavity neck 65 and/or separation tube 15, respectively.

With reference to FIGS. 5A-5D, in an embodiment, groove 87 extends around an outer circumference of plug's lower portion to facilitate a snap fit engagement with cap's retaining lip 70 as plug 25 is inserted into cap 20.

With further reference to FIGS. 5A-5D, in an embodiment, central portion 100 atop plug 25 serves as a mechanical actuator to transition flange 85 between an open position and a closed position. The circumference of central portion 100 is smaller than the circumference of cavity 95, allowing downward displacement of central portion 100. Depression of central portion 100 toward cavity 95 forces flange 85 to invert upward to the open position. Conversely, release of central portion 100 allows flange 85 to relax and return to its native configuration, i.e., the closed position.

Figure 6B:
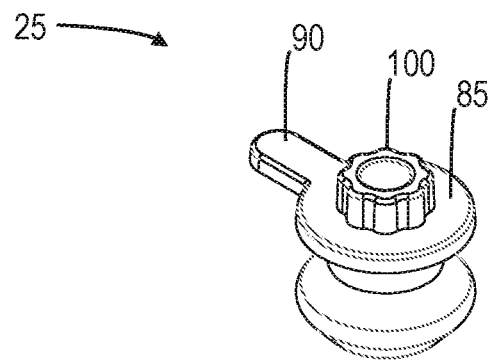
FIGS. 6A-6C show various views of the plug, according to an embodiment of the present invention.
Figure 6C:
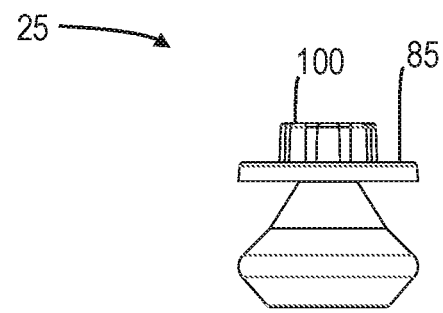
Figure 6A:
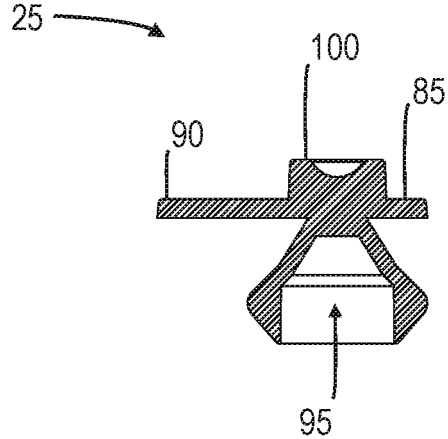
Figure 7:
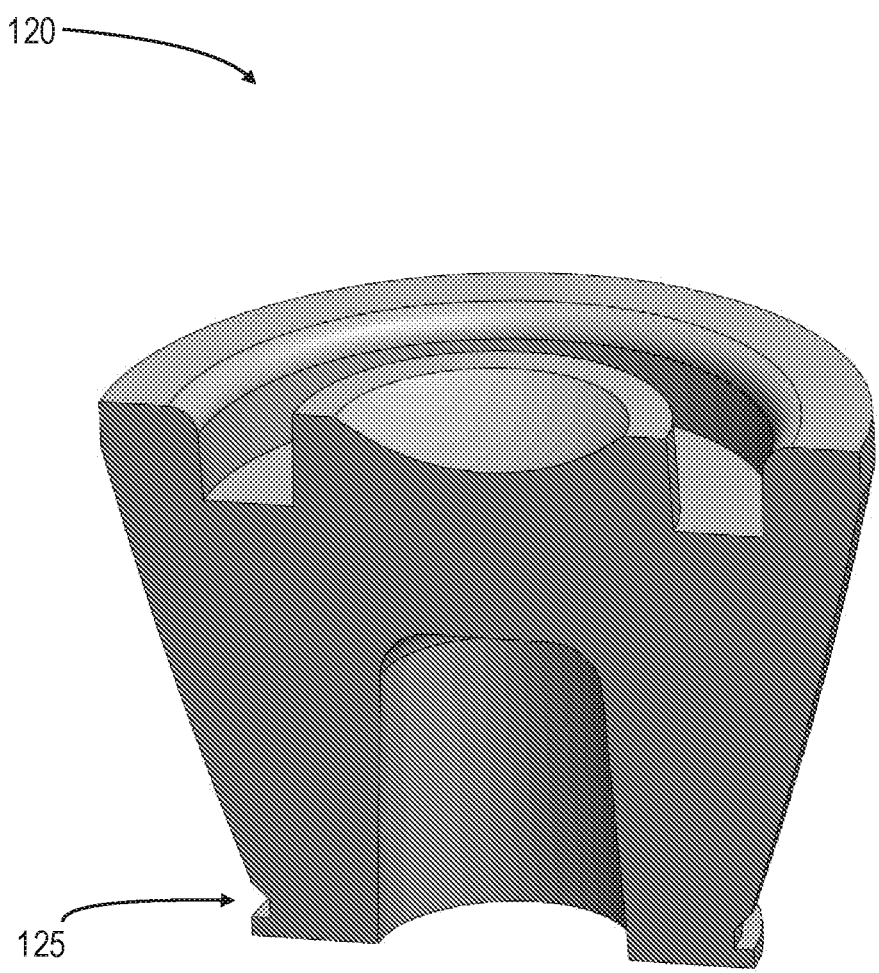
FIG. 7 shows a perspective sectional view of the separation tube's bottom plug, according to an embodiment of the present invention.
Figure 8A:
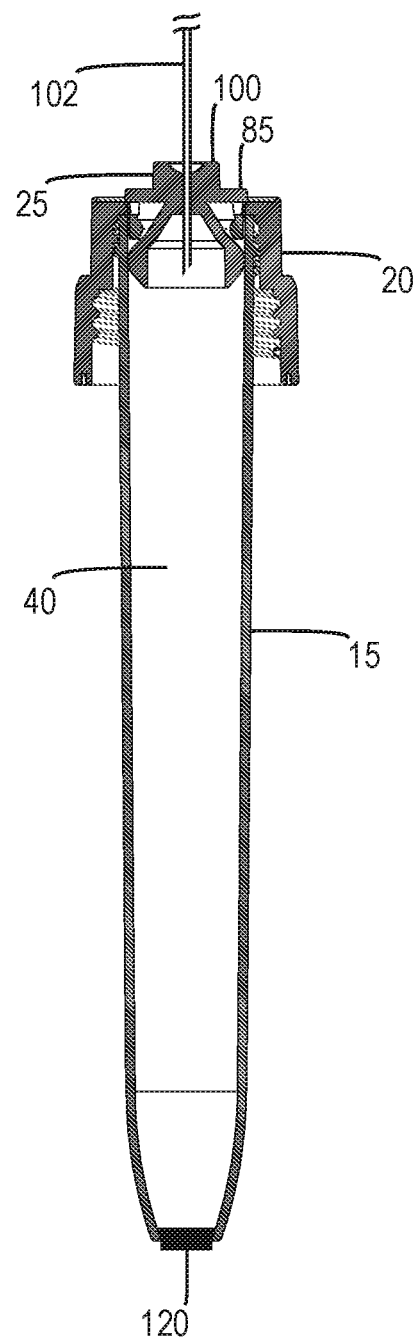
FIG. 8A shows the separation tube, the cap, and the plug with the in an assembled form, according to an embodiment of the present invention.
Figure 8B:
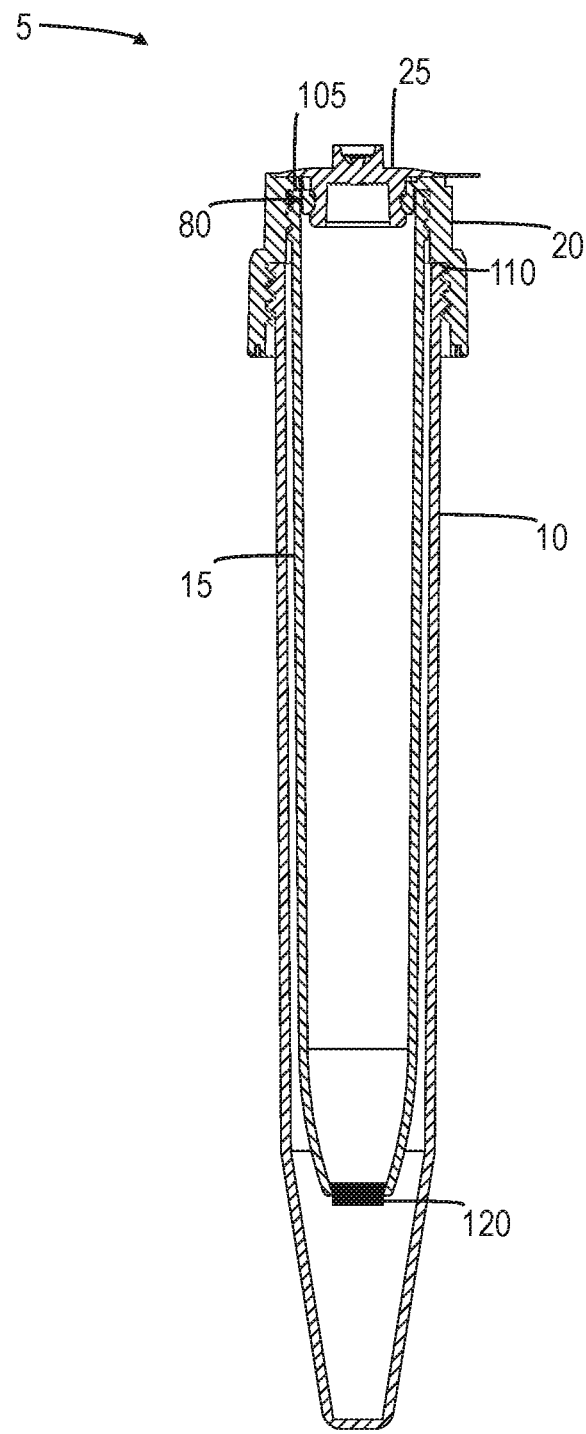

With reference to FIGS. 6A-6C, in an embodiment, the circumference of central portion 100 is larger than the circumference of cavity 95, thus preventing downward displacement of central portion 100. By preventing downward displacement of central portion 100, flange 85 is held in the closed position, i.e., it is unable to transition to the open position. This ensures that channels 75 remain sealed to prevent inadvertent spills or leakage during transport, etc.

In an embodiment, hollow needle 102 is used as a means to introduce air or gas into the upper portion of separation tube 15 through plug 25. Needle 102 is connected to regulator 104. Regulator 104 may be a syringe, a pump, or any other device/machine, e.g., an air compressor, configured to regulate a flow of air, gas, or other matter. This allows air or gas to be introduced into the upper portion of separation tube 15 in a regulated, i.e., controlled and calculable, manner.

Plug 25 is constructed of a flexible and/or compressible material with resilient qualities, e.g., plastic, rubber, or silicone. This facilitates the interference fit between lower portion of plug 25 and a wall surface of cavity neck 65 and/or the interior wall of separation tube 15 by allowing the lower portion of plug 25 to undergo a pre-determined degree of deformation, e.g., compression, during engagement/disengagement with cavity neck 65. Further, it facilitates the process of transitioning flange 85 between its open and closed positions. Additionally, it facilitates penetration of needle 102 through top of plug 25 and into cavity 95 for introducing air or gas into separation tube 15.

In an embodiment, a valve or port (not shown integrated into plug 25. The valve or port provides an alternative means, whereby needle 102, coupled to regulator 104, may be punctured through valve or port, to inject matter, e.g., air, gas, or biological material, into separation tube 15.

In an embodiment, cap 20 is configured without aperture 62, such that the top of cap 20 is closed, i.e., sealed, and, therefore, cap 20 does not require plug 25 to ensure an air-tight seal. In such an embodiment, the interior of separation tube 15 is accessed through cap 20 using one or more valve means. For example, needle 102, coupled to regulator 104, may be punctured through cap 20, or other valve or port (not shown) integrated into cap 20, to inject matter, e.g., air, gas, or biological material, into separation tube 15. At least a portion of cap 20 is preferably constructed of a flexible and/or compressible material with resilient qualities, e.g., plastic, rubber, or silicone, to facilitate penetration of needle 102 through cap 20 and into cavity 95 for introducing matter into separation tube 15.

Referring again to FIG. 1A, assembly of separation apparatus 5 begins with coupling separation tube 15 to cap 20 via engaging connector 45 with connector 60. Once fully engaged, upper edge of separation tube 15 abuts cap ledge 105 to provide a sealed, i.e., air-tight, engagement between cap 20 and separation tube 15. Next, separation tube 15 is received into centrifuge tube 10, and centrifuge tube 10 is coupled to cap 20 via engaging connector 35 with connector 55. Once fully engaged, upper edge of centrifuge tube 10 abuts cap ledge 110 to provide a sealed, i.e., air-tight, engagement between cap 20 and centrifuge tube 10. Next, lower portion of plug 25 is removably inserted into cavity 50. Once fully inserted, lower portion of plug 25 seats into cavity 50, and bottom edge of flange 85 abuts a top surface of cap 20 to provide a sealed, i.e., air-tight, engagement between cap 20 and plug 25. The sealed engagement between cap 20 and plug 25, and cap 20 and separation tube 15, coupled with a means for introducing air or gas into separation tube 15 in a controlled manner, e.g., channels 75 and flange 85, or needle 102 and regulator 104, provides a means for controlled release of liquid from the open bottom of separation tube 15.

With further reference to FIG. 1A, density separation medium 115 is used within separation apparatus 5 to isolate target biological material. Density of density separation medium 115 depends on densities of the material to be separated. For example, to separate target white blood cells from red blood cells, the specific density of density separation medium 115 should be higher than the target white blood cell population. This will allow the higher density red blood cells to sediment through the open bottom of separation tube 15 to the bottom of the centrifuge tube 10. Meanwhile, the lower density white blood cells will remain on top of density separation medium 115 inside of separation tube 15.

With reference to FIGS. 7-9B, in various embodiments, plug 120 is removably engaged to the open bottom of separation tube 15. Engagement between plug 120 and separation tube can be accomplished in a number of ways, including, but not limited to, a friction fit or snap fit. For example, the bottom of separation tube 15 may include a lip for engaging plug channel 125. Plug 120 is constructed of a flexible and/or compressible material with resilient qualities, e.g., plastic, rubber, or silicone. Plug 120 seals the open bottom of separation tube 15 to prevent open communication between cavity 40 and the interior of centrifuge tube 10. Thus, samples can be pipetted onto plug 120, through cap 20, without contacting the density separation medium 115 disposed within centrifuge tube 10. Cap 20 (and, in various embodiments, plug 25) and plug 120 seal separation tube 15, such that cavity 40 can be evacuated (or, at least, partially evacuated). By sealing both ends of separation tube 15 and evacuating cavity 40, separation tube 15 can be used with a multi-needle apparatus used to draw blood (or other biological fluid(s)). Once drawn, separation tube 15 can be used as a transport container prior to the separation process. In various embodiments, the interior wall of separation tube 15 is treated with an agent, e.g., an anti-coagulant, for reacting with a sample.

During centrifugation, plug 120 is configured to disengage from separation tube 15, resulting from the forces exerted onto plug 120 and the surrounding medium/material. Disengagement of plug 120 provides open communication between cavity 40 and the interior of centrifuge tube 10.

Depending on the desired result, plug may be configured/designed to displace inwardly, i.e., into cavity 40, or outwardly, i.e., into centrifuge tube 10, as the forces from centrifugation are exerted onto plug 120 and the surrounding medium/material. Displacement of plug 120 depends on the density of plug 120 relative to the densities of density-separation medium 115 and the various components 130, 135 of the sample containing the target material.

It is useful for plug 120 to release into cavity 40 if the desired target particles have a higher density and/or are substantially larger than unwanted contaminants within the sample/specimen. For illustration purposes, a specimen disposed in separation tube 15 contains target cells and contaminants, e.g., virus particles/cells. The density of the density separation medium 115 disposed in centrifuge tube 10 is lower than the density of the target cells but higher than the unwanted contaminants. Plug 120 has a density that is less than the density of the specimen. Due to increased gravitational forces during centrifugation, and a resultant increase in pressure exerted on the bottom of plug 120 from the density separation medium 115, plug 120 will be displaced into cavity 40 and will float on top of the specimen, thereby providing open communication between separation tube 15 and centrifuge tube 10. As a result of the open communication, a portion of the density separation medium 115 will pass into separation tube 15 through its open bottom. During centrifugation, due to their respective densities, the unwanted contaminants will remain within separation tube 15 on top of the density separation medium 115, i.e., they will not sediment through the density separation medium 115, and the target cells will pass through the density separation medium 115 and sediment in centrifuge tube 10. Even in the case of higher density virus particles/cells, the substantially smaller size of virus particles prevents sedimentation during the time needed to sediment the target cells. Once centrifugation is complete, centrifuge tube 10 can be disengaged from cap 20 for retrieval of the target cells from within centrifuge tube 10.

It is useful for plug 120 to release into centrifuge tube 10, for example, if it is desirable to retain separated target cells within separation tube 15. In such a case, for example, the density of plug 120 has to be higher than the density of the density separation medium 115. During centrifugation, due to its higher density and the resultant gravitational forces, plug 120 will disengage from separation tube 15 and sediment to the bottom of centrifuge tube 10, thus providing open communication between separation tube 15 and centrifuge tube 10. As a result of the open communication, the density separation medium 115 will pass into separation tube 15. The density separation medium 115 will be pre-selected, such that, the unwanted particles/cells, e.g., erythrocytes, have a higher density than the density separation medium 115, and the target cells, e.g., mononuclear cells like lymphocytes, have a lower density than the density separation medium 115. Thus, the unwanted particles/cells will sediment through the density separation medium 115 to the bottom of the centrifuge tube 10 whereas, the target cells will sediment on top of the density separation medium inside of separation tube 15. Once centrifugation is complete, the target cells can be retrieved from separation tube 15 either through cap 20 or by disengaging centrifuge tube 10 from cap and dispensing the target material through the open bottom of separation tube 15 as described herein.

Method(s) of Use

FIG. 10 outlines various methods of using the separation system, according to various embodiments of the present invention. At step 200, a pre-determined volume of density separation medium 115 is deposited into separation apparatus 5. This can be accomplished, for example, by depositing density separation medium 115 into centrifuge tube 10, followed by inserting separation tube 15, coupled to cap 20, into centrifuge tube 10 and coupling centrifuge tube 10 to cap 20. Where plug 120 is not employed, i.e., where open communication exists between the interior of centrifuge tube 10 and cavity 40, density separation medium 115 passes into separation tube 15 through the open bottom of separation tube 15. As another example, separation tube 15, coupled to cap 20, can be inserted into centrifuge tube 10, followed by coupling centrifuge tube 10 to cap 20 and depositing density separation medium 115 into separation tube 15 through cavity 50, whereby density separation medium 115 flows into centrifuge tube 10 through the open bottom of separation tube 15. The amount of density separation medium 115 deposited into separation apparatus 5 is such that, a lower portion of separation tube 15 is submersed in and, in embodiments that do not employ plug 120, filled with density separation medium 115.

At step 205, a sample containing biological material is deposited into separation tube 15. Where plug 120 is employed, a sample may be pipetted onto plug 120 through cap 20. This could be accomplished, for example, by puncturing needle 102 through cap 20 (or plug 25) and dispensing the sample through needle 102 into separation tube 15 or, alternatively, by depositing the sample into separation tube 15 through cap 20 via aperture 62. Alternatively, where cavity 40 is evacuated, one end of a blood-drawing needle apparatus is inserted into a patient's vein, and the opposite end of the needle apparatus is punctured through cap 20 (or plug 25), whereby the vacuum in cavity 40 draws the blood sample through the needle apparatus into separation tube 15. The blood flow stops at a certain volume, i.e., when the pressure within separation tube 15 equals the blood pressure in the vein. The anticoagulant disposed on the interior walls of separation tube 15 prevents blood entering separation tube 15 from clotting.

Alternatively, at step 205, where plug 120 is not employed, the sample is deposited on top of density separation medium 115 within cavity 40. This could be accomplished, for example, by puncturing needle 102 through cap 20 and dispensing the sample through needle 102 into separation tube 15 or, alternatively, by depositing the sample into separation tube 15 through cavity 50 via aperture 62.

At step 210, in an embodiment in which aperture 62 extends through a top surface of cap 20, plug 25 is engaged with cap 20 to ensure a complete air-tight seal of separation apparatus 5. At step 215, separation apparatus 5 containing density separation medium 115 and the sample is placed in a centrifuge and the sample is centrifuged.

In various embodiments in which plug 120 is employed, during centrifugation, plug 120 is disengaged from the open bottom of separation tube 15, thereby providing open communication between an interior of centrifuge tube 10 and cavity 40, whereby the density separation medium 115 comes in contact with the sample, allowing the various components to separate according their specific weight. For example, depending on the density of the density separation medium 115, red blood cells may sediment through the density separation medium 115 through the open bottom of separation tube 15 and deposit at the bottom of centrifuge tube 10; whereas, cells with lower density will remain on top of the density separation medium 115 inside separation tube 15. Thus, based on known densities of the target material, density separation medium 115 may be strategically selected to manipulate the final placement of the target material (i.e., either in separation tube 15 or centrifuge tube 10) for collection, post-centrifugation.

With reference to FIGS. 11A-12C, following centrifugation, at step 220, centrifuge tube 10 is removed from cap 20, and separation tube 15 remains connected to cap 20. The sealed, i.e., air-tight engagement between cap 20 and separation tube 15 (and cap 20 and plug 25 where plug 25 is employed) prevents liquid or other material from spontaneously flowing out of the lower end of separation tube 15. By sealing the top of separation tube 15, air is prevented from entering and exerting a downward force on liquid inside separation tube 15, leaving only the upward force of atmospheric pressure being exerted on the liquid at the open bottom. As such, the pressure inside separation tube 15 is less than the external atmospheric pressure. Further, the upward force of atmospheric pressure is greater than the force of gravity pulling down on the liquid. Thus, the liquid is held inside separation tube 15.

At step 225, air or gas is introduced into the upper portion of separation tube 15. This increases the pressure inside separation tube 15, such that it is equal to or greater than the external atmospheric pressure. Air or gas can be introduced into separation tube 15 in a number of ways. For example, in an embodiment, pressure is applied to plug 25 to transition flange 85 to its open position, allowing an in-flow of air through channels 75 and into separation tube 15. The degree of inversion is dependent on the amount of pressure applied to plug 25. As such, the volume of influent air can be controlled by adjusting the amount of pressure exerted on plug 25. As air enters the top of separation tube 15, the upward and downward forces of air pressure on the liquid equalizes, leaving gravity as the dominant force causing the liquid to drop out of the bottom of separation tube 15. As air is introduced into separation tube 15, a corresponding volume of liquid is expelled through the lower end of separation tube 15. Therefore, the release of liquid from separation tube 15 can be controlled by adjusting the amount of pressure exerted on cap 20.

In another embodiment, needle 102 is punctured into and through plug 25 and air or gas is introduced into the upper portion of separation tube 15 through needle 102. Needle 102 is connected to regulator 104, such that the air or gas can be introduced into the upper portion of separation tube 15 in a regulated manner. The regulated influx of air or gas defines the release speed of the fluid from the open bottom of separation tube 15. As air or gas is introduced into separation tube 15, a corresponding volume of liquid is expelled through the lower end of separation tube 15. Therefore, the release of liquid from separation tube 15 can be controlled by adjusting the amount of air or gas injected into separation tube 15.

At step 230, air- or gas-flow into separation tube 15 is halted. This is accomplished, for example, by releasing pressure from plug 25, allowing flange 85 to revert to its native configuration, i.e., the closed position, thereby sealing channels 75 and preventing additional air from flowing into separation tube 15. Similarly, air or gas-flow through needle 102 may be shut off. By halting air- or gas-flow into separation tube 15, the pressure inside separation tube 15 drops below the external atmospheric pressure, preventing release of any remaining fluid inside from separation tube 15 until air- or gas-flow resumes.

Optionally, at step 235, the efflux from separation tube 15 is analyzed, based on characteristics including, but not limited to, light absorption, emission, refraction, reflection and diffraction.

While the foregoing method is described and shown in a numerical, step-wise order, it should be understood that the steps are not limited to any specific order. Additionally, some steps may overlap in time, i.e., they may be carried out simultaneously, with other steps.

The invention has been described herein using specific embodiments for the purposes of illustration only. It will be readily apparent to one of ordinary skill in the art, however, that the principles of the invention can be embodied in other ways. For example, one skilled in the art would understand and appreciate that any connection means, e.g., threading, interference fit, snap fit, etc., described herein and/or shown in the drawings, could be substituted with another connection means capable of performing the same function. Similarly, one skilled in the art would understand and appreciate that placement of connection means, e.g., interiorly-located vs. exteriorly-located, could be reversed without deviating from the scope of the present invention. Likewise, it will be readily apparent that the features, functions, and/or elements of the present invention disclosed herein can be used in any combination to produce various embodiments of the present invention. Therefore, the invention should not be regarded as being limited in scope to the specific embodiments disclosed herein, but instead as being fully commensurate in scope with the following claims.

I claim:

1. A method for separating and collecting a target material from a fluid sample comprising:
    providing an apparatus comprising a centrifuge tube, a separation tube having an open bottom, and a cap, wherein the centrifuge tube and the separation tube are configured to sealingly and releasably couple to the cap such that a pre-determined length of the separation tube is positioned within the centrifuge tube, and a density separation medium disposable within the centrifuge tube and the separation tube, wherein a volume of the density separation medium is such that, when the separation tube and the centrifuge tube are coupled to the cap, the open bottom of the separation tube is submersed in the density separation medium;
    depositing the fluid sample on top of the density separation medium inside of the separation tube;
    centrifuging the apparatus with the fluid sample;
    introducing air or gas into the separation tube utilizing a hollow needle operably coupled to a regulator configured to regulate a flow of matter and wherein the cap is configured to receive the needle therethrough; and
    halting air- or gas-flow into the separation tube such that a target material is separated from the fluid sample, and collecting the separated target material from the separation tube.

2. The method of claim 1, wherein the needle is operably coupled to a regulator selected from the group consisting of: a syringe, a pump, and an air compressor.

3. The method of claim 1, wherein the needle is punctured through the cap.

4. The method of claim 3, wherein the cap is constructed of a flexible material.

5. The method of claim 1, wherein the cap comprises a resealable valve or port integrated therewith configured to allow the needle to be inserted therethrough and reseal after the needle is removed from the cap.

6. The method of claim 1, wherein a top of the cap comprises an aperture that opens into a cavity of the cap and further comprises a plug that is configured to releasably seal the aperture.

7. The method of claim 6, wherein the needle is punctured through the plug.

8. The method of claim 7, wherein the plug is constructed of a flexible material.

9. The method of claim 6, wherein the plug comprises a resealable valve or port integrated therewith configured to allow the needle to be inserted therethrough and reseal after the needle is removed from the plug.

10. The method of claim 1, wherein as air or gas is introduced into the separation tube through the needle, a corresponding volume of the fluid sample is controllably expelled through the open bottom of the separation tube.

11. The method of claim 1, further comprising uncoupling the centrifuge tube from the cap once centrifugation is complete, wherein the target material is retained within the separation tube.

12. The method of claim 1, further comprising re-introducing air or gas into the separation tube utilizing the hollow needle after halting the air- or gas-flow.

13. The method of claim 1, wherein introducing air or gas into the separation tube results in a pressure inside of the separation tube being equal to or greater than an external atmospheric pressure surrounding the apparatus.

14. The method of claim 1, wherein when coupled to the cap, an area between an exterior surface of the separation tube and an interior surface of the centrifuge tube is unobstructed along the pre-determined length.

\* \* \* \* \*